(12) United States Patent
Kuboki et al.

(10) Patent No.: US 6,420,464 B1
(45) Date of Patent: Jul. 16, 2002

(54) POLYHYDRIC PHENOL COMPOUNDS, EPOXY RESINS, EPOXY RESIN COMPOSITIONS AND CURED PRODUCTS THEREOF

(75) Inventors: Kenichi Kuboki, Matsudo; Yoshitaka Kajiwara, Yono; Eiko Watanabe, Tokyo; Yoshio Shimamura, Toride; Katsuhiko Oshimi, Yono, all of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/486,165

(22) PCT Filed: Jun. 24, 1998

(86) PCT No.: PCT/JP98/02812

§ 371 (c)(1),
(2), (4) Date: Apr. 24, 2000

(87) PCT Pub. No.: WO99/67233

PCT Pub. Date: Dec. 29, 1999

(51) Int. Cl.[7] .................................................. C08K 5/15
(52) U.S. Cl. ........................ 524/109; 524/324; 524/339; 524/341; 528/196; 534/557; 430/191; 430/192; 430/193
(58) Field of Search .......................... 534/557; 528/196; 430/191, 192, 193; 524/109, 324, 339, 341

(56) References Cited

U.S. PATENT DOCUMENTS

| | | | |
|---|---|---|---|
| 5,514,515 A | 5/1996 | Zampini et al. | 430/192 |
| 5,840,646 A | 11/1998 | Katayama et al. | 502/152 |

FOREIGN PATENT DOCUMENTS

| | | |
|---|---|---|
| EP | 0 761 694 | 3/1997 |
| FR | 2163325 | 7/1973 |
| JP | 8-269037 | 10/1996 |
| JP | 8-339075 | 12/1996 |

*Primary Examiner*—Kriellion A. Sanders
(74) *Attorney, Agent, or Firm*—Nields & Lemack

(57) ABSTRACT

Resin compositions having a low viscosity, a low hygroscopicity, high adhesive properties and a high heat resistance as well as being light in weight and excellent in mechanical properties are provided. The resin compositions include polyhydric phenol compounds represented by the formula (1) and epoxy resins represented by the formula (3).

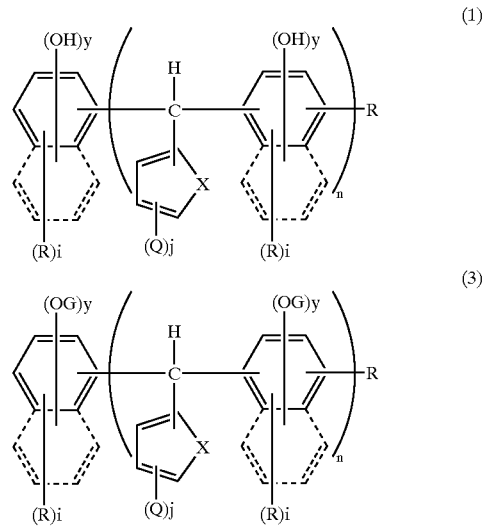

7 Claims, 2 Drawing Sheets

POLYHYDRIC PHENOL COMPOUNDS, EPOXY RESINS, EPOXY RESIN COMPOSITIONS AND CURED PRODUCTS THEREOF

FIELD OF THE INVENTION

The present invention relates to polyhydric phenol compounds and epoxy resins obtained by glycidyl etherification thereof, which are suitable for use in various kinds of materials of plastics (polycarbonate, PEEK, PPO, polysulfone, etc.); materials of thermosetting resins (epoxy resin, cyanate resin, acrylate resin, etc.); antioxidants; insulating materials for electric and electronic parts including highly reliable sealing compounds for semiconductors; various composite materials including laminated sheets (printed-wiring boards) and CFRP (carbon fiber-reinforced plastics); components of adhesive compositions, coating compositions and molding compositions; as well as various industrial intermediates.

BACKGROUND OF THE INVENTION

Polyhydric phenol compounds have actually a wide variety of applications in the fields of thermoplastic materials, thermosetting resin materials, insulating materials for electric and electronic parts, structural materials, components of adhesive compositions and coating compositions, as well as antioxidants.

In recent years, however, polyhydric phenol compounds have been applied to a wide variety of uses and requested to satisfy more diversified property requirements, which conventional compounds such as bisphenol A, bisphenol F, phenolic novolak and cresol novolak would fail to meet. For the purpose of satisfying these new property requirements, many polyhydric phenol compounds have been synthesized. In the fields of electric and electronic parts, in particular, there is a need for curable resin compositions and cured products thereof having a low viscosity, a low hygroscopicity and high adhesive properties, but such need remains unsatisfied.

On the other hand, epoxy resins obtained by glycidyl etherification of polyhydric phenol compounds, by virtue of having good working properties of their own as well as by virtue of having excellent electrical properties, a high heat resistance, good adhesive properties and a high moisture resistance (water resistance) in the form of cured products thereof, are widely used in the fields of electric and electronic parts, structural materials, adhesive compositions, coating compositions and the like.

With the recent development of electrics and electronics, however, these fields are in need of resins having more improved properties including a higher purity, a higher moisture resistance, better adhesive properties and a lower viscosity permitting a high packing density of filler. Also, lightweight materials having excellent mechanical and physical properties are needed as structural materials for use in aerospace industries and equipments for leisure time amusement and sports. In an attempt to meet these requirements, many improvements of epoxy resins and epoxy-containing resin compositions have been proposed, but these requirements still remain unsatisfied.

SUMMARY OF THE INVENTION

The present inventors, with the intention of solving the problems set forth above, have eagerly studied on novel polyhydric phenol compounds and epoxy resins obtained by glycidyl etherification thereof and accomplished the present invention.

More specifically, the present invention relates to:

(1) a polyhydric phenol compound represented by the formula (1):

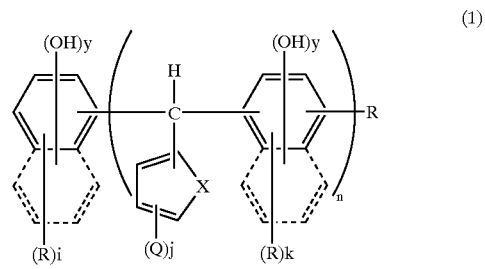

wherein, X represents an oxygen or sulfur atom; Q represents a hydrogen atom or a C1–C5 alkyl group; R represents a hydrogen atom, a C1–C10 hydrocarbon group, an alkoxy group or a halogen atom; i is an integer of 1 to 6; j is an integer of 1 to 3; k is an integer of 1 to 5; and y is an integer of 1 to 2; n is an average number and represents a real number of 1 to 15;

(2) the polyhydric phenol compound as defined in the above item (1), characterized in that it is represented by the formula (2):

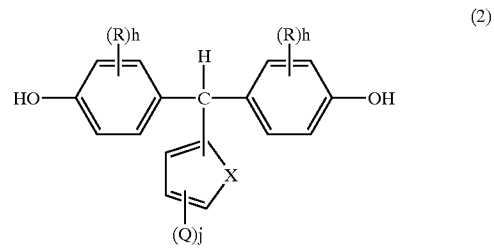

wherein X, Q, R and j are of the same meanings as defined in the formula (1); and h is an integer of 1 to 4;

(3) the polyhydric phenol compound as defined in the above item (1) or (2), wherein X in the formula (1) represents an oxygen atom;

(4) the polyhydric phenol compound of any one of the above items (1) to (3), wherein n represents a number of not less than 1.5 and less than 10;

(5) a process for producing a polyhydric phenol compound comprising condensing a phenol with a compound of the formula (a):

wherein X, Q and j are of the same meanings as defined in the formula (1), in the presence of a basic catalyst;

(6) the process as defined in the above item (5), wherein the phenol is 2, 6-xylenol;

(7) the process as defined in the above item (5), wherein the phenol is 2, 5-dialkylphenol;

(8) the process as defined in any one of the above items (5) to (7), wherein the basic catalyst is at least one compound selected from the group consisting of alkaline metal oxides, alkaline earth metal oxides, alkaline metal alkoxides and alkaline earth metal alkoxides;

(9) an epoxy resin represented by the formula (3):

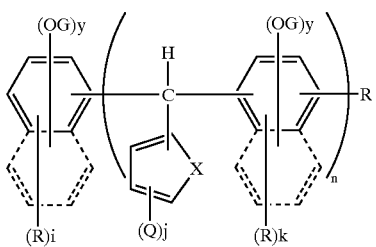

wherein G represents a glycidyl group and R, Q, X, n, y, i, j and k are of the same meanings as defined in the formula be (1);

(10) an epoxy resin represented by the formula (4):

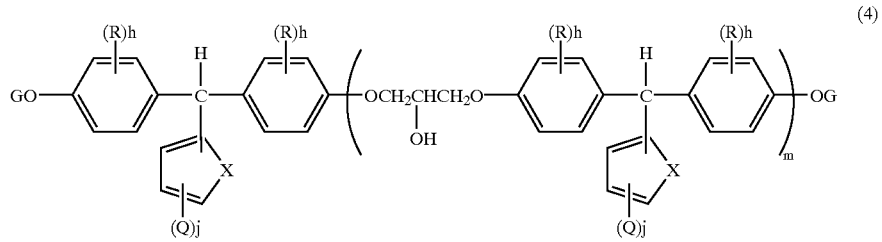

wherein G, R, Q, X and j are of the same meanings as defined in the formula (3); m is an average value and represents a real number of 0 to 20; and h represents an integer of 1 to 4;

(11) a thermosetting resin composition containing a polyhydric phenol compound as defined in anyone of the above items (1) to (3) and/or an epoxy resin as defined in the above item (9) or (10);

(12) a cured product obtained by curing the thermosetting resin composition of the above item (11);

(13) a semiconductor device fabricated by incorporating the thermosetting resin composition as defined in the above item (11);

(14) a thermoplastic material fabricated by starting with a polyhydric phenol compound as defined in any one of the above items (1) to (3).

DETAILED DESCRIPTION OF THE INVENTION

Figure 1:
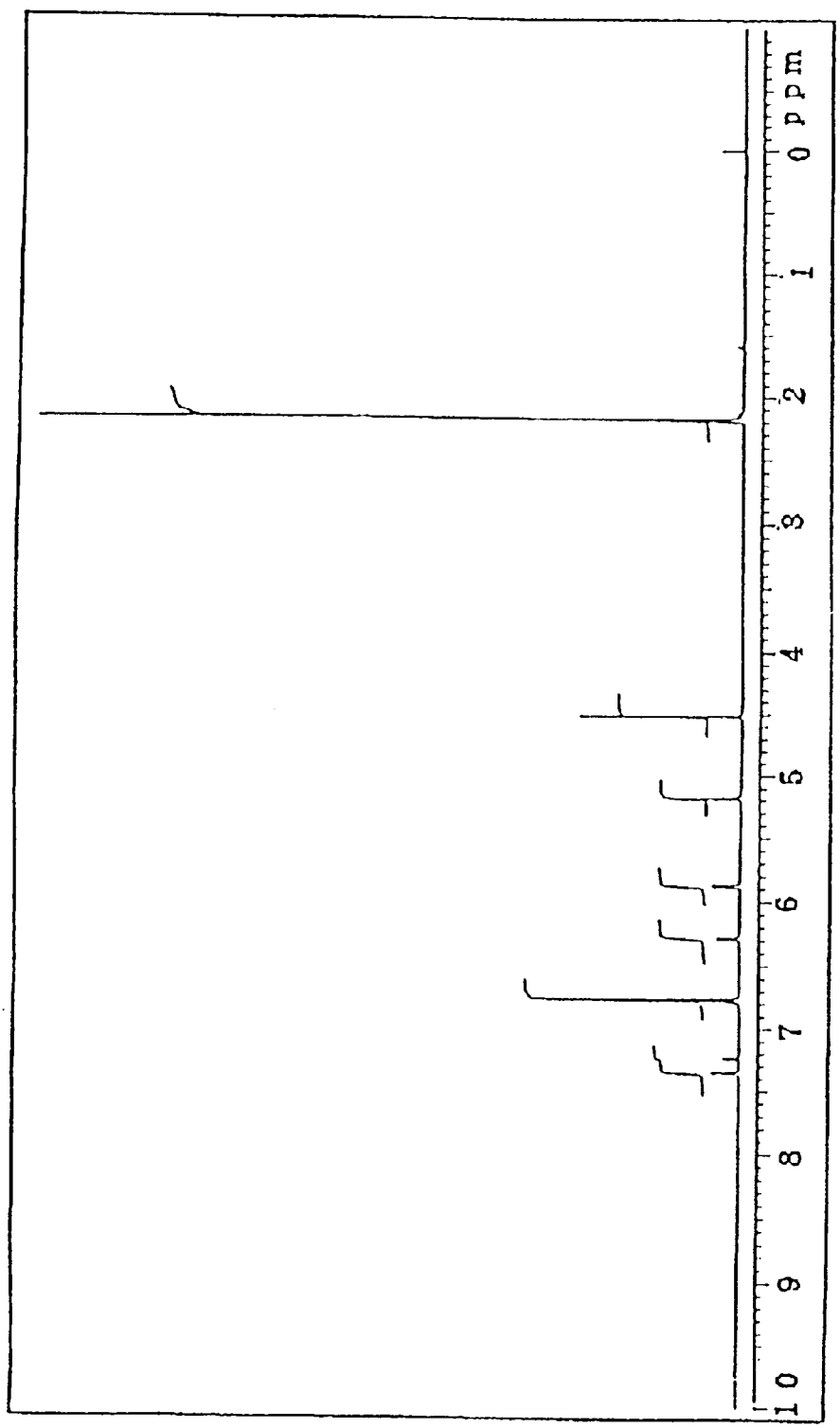
FIG. 1 represents the $^1$H-NMR spectra of the polyhydric phenol compound of the present invention (P1) obtained in Example A1.

Polyhydric phenol compounds of the present invention can be obtained by polycondensing a phenol with a compound of the formula (a) in the presence of a catalyst with or without a solvent.

Examples of compounds of the formula (a) which can be used are furfural, 3-furaldehyde, 3-methylfurfural, 5-methylfurfural, 5-ethylfurfural, 2-thiophene-carboxyaldehyde, 3-thiophenecarboxyaldehyde, 3-methyl-2-thiophenecarboxy-aldehyde and the like, among which those of the formula (a) wherein X represents an oxygen atom are particularly preferred. Compounds of the formula (a) are not limited to those cited above and can be used alone or as a mixture of two or more.

Phenols which may be mentioned are phenol, cresol, xylenol (dimethylphenol) such as 2,6-xylenol, trimethylphenol, 2,5-alkylphenol such as 2-tert-butyl-5-methyl-phenol, 2-tert-butyl-4-methylphenol, allylphenol, octylphenol, phenylphenol, diphenylphenol, guaiacol, hydroquinone, resorcin, catechol, naphthol, dihydroxynaphthalene, methyl naphthol, allylphenol and the like, among which 2,6-xylenol or 2,5-alkylphenol is preferred. Phenols are not limited to those cited above and can be used alone or as a mixture of two or more. Phenols may be used in an amount of generally 1.5 to 20 moles, preferably 1.8 to 10 moles per 1 mole of the compound of the formula (a).

Solvents which can be mentioned include, but are not limited to, methanol, ethanol, propanol, isopropanol, toluene, xylene and the like, which can be used alone or as a mixture of two or more. When required, solvent may be used in an amount of generally 5 to 500 parts by weight, preferably 10 to 300 parts by weight per 100 parts by weight of phenols.

Preferred catalysts are basic compounds. Polycondensation can proceed also in the presence of acidic catalysts, but acidic catalysts may give rise to the mutual reaction of the compound of the formula (a), resulting in the increase of by-products. Organic metallic compounds can also be used as catalysts, but they are not favorable in respect of cost. Examples of the basic catalysts which can be used include, but are not limited to, alkaline metal hydroxides such as lithium hydroxide, sodium hydroxide, potassium hydroxide, etc.; alkaline earth metal hydroxides such as magnesium hydroxide, calcium hydroxide, etc.; alkaline metal alkoxides such as sodium methoxide, sodium ethoxide, potassium methoxide, potassium ethoxide, potassium-tert-butoxides, etc.; and alkaline earth metal alkoxides such as magnesium methoxide, magnesium ethoxide, etc. These catalysts can be used alone or in combination of two or more. Catalysts can be used in an amount of generally 0.005 to 2.0 moles, preferably 0.01 to 1.1 moles per 1 mole of phenols.

Reaction may be carried out by adding a catalyst to a mixture of a compound of the formula (a) with a phenol (and optionally a solvent) and heating the resulting mixture. Alternatively, to a mixture of a phenol and a catalyst (and optionally a solvent) under heating, a compound of the formula (a) may be gradually added. The reaction time ranges from 5 to 100 hours and the reaction temperature ranges from 50 to 150° C. After the reaction has completed, the reaction mixture is neutralized. Then, unreacted materials and solvents are removed off by filtration or by heating in vacuum, to afford a polyhydric phenol compound of the present invention.

If the obtained polyhydric phenol compounds are polymeric compounds of the formula (1) wherein n is more than 0, those of the formula (1) wherein n is not less than 1.5 and less than 10 are preferred.

Polyhydric phenol compounds of the present invention represented by the formula (2) can be obtained by purifying the compound of the formula (1) produced in the manner as stated above.

Alternatively, compounds of the formula (1) can be synthesized by selecting as a starting phenol the specified phenols such as 2,6-dialkylphenol, 2,3,6-trialkylphenol, and 2,3,5,6-tetraalkylphenol. The obtained compounds can be used as a starting material of an epoxy resin or cyanate ester resin with an improved reactivity or can be used as a curing agent of an epoxy resin or cyanate ester resin having an improved curability attributable to an improved reactivity.

The polyhydric phenol compounds of the present invention obtained in the manner as stated above are useful as starting materials of plastics as such or can be used in the form of thermosetting resin compositions as described hereinafter.

Epoxy resins of the present invention will now be more specifically described.

An epoxy resin of the present invention represented by the formula (3) can be obtained by reaction of a polyhydric phenol compound of the present invention represented by the formula (1) with an epihalohydrin in the presence of an alkaline metal hydroxide.

Examples of epihalohydrins which can be used are epichlorohydrin, epibromohydrin, epiiodohydrin, β-methylepichlorohydrin, β-methylepibromohydrin, β-ethylepichlorohydrin and the like. Epichlorohydrin is particularly preferred, since being industrially available at a reasonable price. This reaction can be conducted in accordance with previously known processes.

By way of example, a mixture of a compound of the formula (1) and an epihalohydrin is allowed to react at a temperature of 20 to 120° C. for 1 to 20 hours while adding collectively in one lot or gradually by portions a solid alkaline metal hydroxide, e.g. potassium hydroxide. The alkaline metal hydroxide may be used in the form of aqueous solution. In such cases, while adding continuously the alkali metal hydroxide to the reaction system, water and epihalohydrin may be allowed to distill off continuously under reduced pressure or normal pressure. Then, the distillate may be separated into water and epihalohydrin so that the water may be removed out of the reaction system and the epihalohydrin may be recycled continuously into the reaction system.

In the process described above, epihalohydrins are used in an amount of generally 0.5 to 20 moles, preferably 0.7 to 10 moles per 1 equivalent of hydroxyl group in the compound of the formula (1). Alkali metal hydroxides are used in an amount of generally 0.5 to 1.5 moles, preferably 0.7 to 1.2 moles per 1 equivalent of hydroxyl group in the compound of the formula (1). When an aprotic polar solvent such as dimethylsulfone, dimethylsulfoxide, dimethylformamide, 1,3-dimethyl-2-imidazolidine and the like is added to the above reaction, an epoxy resin having a low content of saponifiable halogen and hence being suitable as sealing compound for electronics can be obtained. Aprotic polar solvents may be used in an amount of generally 5 to 200% by weight, preferably 10 to 100% by weight on the basis of the weight of epihalohydrins. Addition of other solvents than those that were cited above, e.g. alcoholic solvents such as methanol, ethanol, etc. might facilitate the reaction. Toluene, xylene, dioxane and the like are also usable as solvents.

Alternatively, an epoxy resin of the present invention can be obtained by reacting a mixture of a compound of the formula (1) with an excessive amount of epihalohydrin at 50 to 150° C. for 1 to 20 hours in the presence of a catalyst comprising a quaternary ammonium salt selected from tetramethylammonium chloride, tetramethylammonium bromide, trimethylbenzyl ammonium chloride and the like, to afford a halohydrin ether of the compound of the formula (1), to which an alkaline metal hydroxide such as sodium hydroxide or potassium hydroxide in the form of solid or aqueous solution is added and the resulting mixture is allowed to react at 20 to 120° C. for 1 to 20 hours so as to induce cyclization of the halohydrin ether. The quaternary ammonium salt may be used in an amount of generally 0.001 to 0.2 mole, preferably 0.05 to 0.1 mole per 1 equivalent of hydroxyl group in the compound of the formula (1).

In general, these reaction products, with or without washing with water, are heated in vacuum for removing the excess of epihalohydrins, dissolved in a solvent such as toluene, xylene, methylisobutylketone, etc. and allowed to react again with the addition of an aqueous solution of alkaline metal hydroxide such as sodium hydroxide, potassium hydroxide, etc. Alkaline metal hydroxides may be used in an amount of generally 0.01 to 0.2 mole, preferably 0.05 to 0.1 mole per 1 equivalent of hydroxyl group in the compound of the formula (1). The reaction temperature generally ranges from 50 to 120° C. and the reaction time generally ranges from 0.5 to 2 hours.

After reaction has completed, the reaction mixture may be treated by filtration or washed with water for removing by-produced salts and heated in vacuum for distilling off the solvent such as toluene, xylene, methylisobutylketone, to afford an epoxy resin having a low content of saponifiable halogen.

Alternatively, the synthesis step and the epoxidation step of a compound of the formula (1) can be conducted continuously. By way of example, a compound of the formula (a) is made to react with a phenol by the process described above. Then, without removing unreacted starting materials nor solvents, e.g. without subjecting the reaction system to neutralization, filtration nor distillation under heating in vacuum, an epihalohydrin is directly added to the reaction system so that epoxidation may proceed in accordance with the process described above. Epoxides of unreacted phenols may be distilled off together with the solvents in the final step of distilling off the solvents.

Further, an epoxy resin of the present invention represented by the formula (4) can be obtained by epoxidizing a compound of the formula (2) in the same way as stated above. As a smaller amount of epihalohydrin is used, a compound having a greater value of m can be obtained.

Thermosetting resin compositions will now be described. Polyhydric phenol compounds of the present invention can act as a curing agent for epoxy resins and/or cyanate ester resins, etc. and for that purpose, can be used alone or in combination with other curing agent. When used in combination, polyhydric phenol compounds are contained in a proportion of preferably not less than 10% by weight, more preferably not less than 20% by weight on the basis of the total weight of the curing agent.

Examples of other curing agents which can be used in combination with phenol resins of the present invention are amine compounds, acid anhydride compounds, amide compounds, phenol compounds and the like. Examples of other curing agents which can be used are diaminodiphenylmethane, diethylenetriamine, triethylenetetramine, diaminodiphenyl-sulfone, isophoronediamine, dicyanodiamide, polyamide resin synthesized from linolenic dimer and ethylenediamine, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, bisphenols, polycondensates of phenols (phenol, alkyl-substituted phenol, naphthol, alkyl-substituted naphthol, dihydroxybenzene, dihydroxynaphthalene, etc.) with various aldehydes, polymers of phenols with various diene compounds, polycondensates of phenols with aromatic dimethylols, biphenols and modified biphenols, imidazole, $BF_3$-amine complex, guanidine derivatives and the like.

As examples of epoxy resins which can be used in thermosetting resin compositions of the present invention, there can be mentioned epoxy resins of the present invention and other epoxy resins including: glycidyl ether epoxy resins obtained by glycidyl etherification of bisphenols, polycondensates of phenols (phenol, alkyl-substituted phenol, naphthol, alkyl-substituted naphthol, dihydroxybenzene, dihydroxynaphthalene, etc.) with various aldehydes, polymers of phenols with various diene compounds, polycondensates of phenols with aromatic dimethylols, alcohols and the like; alicyclic epoxy resins; glycidyl amine epoxy resins; glycidyl ester epoxy resins; and the like. But, without limiting to those cited above, any of conventionally used epoxy resins can be used. These epoxy resins can be used alone or in combination of two or more.

When epoxy resins of the present invention are used in thermosetting resin compositions of the present invention, the curing agents thereof may comprise polyhydric phenol compounds or other curing agents as cited above which can be used alone or in combination of two or more.

Alternatively, when epoxy resins of the present invention are used in thermosetting resin compositions of the present invention, the epoxy resins of the present invention can be used alone or in combination with other epoxy resins as cited above. When used in combination with other epoxy resins, the epoxy resins of the present invention may be present in a proportion of preferably not less than 20% by weight, more preferably not less than 30% by weight on the basis of the total weight of epoxy resins.

When thermosetting resin compositions of the present invention are containing epoxy resins commonly used cure accelerators for epoxy resins may be incorporated thereinto as desired. Cure accelerators which can be mentioned include imidazole compounds such as 2-methylimidazole, 2-ethylimidazole, etc., boron trifluoride complex, phosphorus compounds such as triphenylphosphine, trioctylphosphine, etc. and can be used in an amount of 0.01 to 15 parts by weight, preferably 0.1 to 10 parts by weight on the basis of 100 parts by weight of epoxy resins.

Examples of cyanate ester resins which can be used in thermosetting resin compositions of the present invention include, but are not limited to, dicyanatobenzene, tricyanatobenzene, dicyanatonaphthalene, dicyanatobiphenyl, 2,2'-bis(4-cyanatephenyl)propane, bis (4-cyanatephenyl)-methane, bis(3,5-dimethyl-4-cyanatephenyl)methane, 2,2'-bis(3,5-dimethyl-4-cyanatephenyl)propane, 2,2'-bis (4-cyanatephenyl)ethane, 2,2'-bis(4-cyanatephenyl)hexachloro-propane, bis(4-cyanatephenyl)sulfone, bis(4-cyanatephenyl)-thioether, phenolic novolak cyanate, phenol/dicyclopentadiene co-condensates having a hydroxyl group replaced by a cyanate group and the like.

When thermosetting resin compositions of the present invention are containing cyanate resins, there can be incorporated as desired a catalyst for trimerizing a cyanate group to form a sym-triazine ring. The catalyst may be selected from zinc naphtenate, cobalt naphtenate, copper naphtenate, lead naphtenate, zinc octylate, tin octylate, lead acetylacetonate, dibutyltin maleate and the like. Catalysts are used in an amount of generally 0.0001 to 0.10 parts by weight, preferably 0.00015 to 0.0015 parts by weight on the basis of 100 parts by weight of thermosetting resin compositions.

In order to impart flame retardant properties to the cured products obtained by curing thermosetting resin compositions of the present invention, glycidyl ether of tetrabromobisphenol A or brominated phenolic novolak epoxy resins may be used in combination. These epoxy resins may be blended in such an amount that the cured products may have a bromine content of generally 10 to 40% by weight, preferably 12 to 35% by weight and more preferably 15 to 27% by weight.

Thermosetting resin compositions of the present invention may contain either one or both of epoxy resins and cyanate ester resins as cited above.

In thermosetting resin compositions of the present invention, curing agents can be used in an amount of generally 0.5 to 1.5 equivalents, preferably 0.6 to 1.2 equivalents per 1 equivalent of epoxy resins and generally 0.5 to 1.5 equivalents, preferably 0.6 to 1.2 equivalents per 1 equivalent of cyanate ester resins.

Further, thermosetting resin compositions of the present invention can be blended with known additives as desired. Examples of additives which can be used are polybutadiene and modified polybutadiene, modified acrylonitrile copolymer, polyphenylene ether, polystyrene, polyethylene, polyimide, fluorocarbon resin, maleimide compound, silicone gel, silicone oil, as well as inorganic fillers such as silica, alumina, calcium carbonate, quartz powder, aluminum powder, graphite, talc, clay, iron oxide, titanium oxide, aluminum nitride, asbestos, mica, glass powder, glass fiber, non-woven glass fabric or carbon fiber, etc., surface treatment agents of fillers such as silane coupling agents, mold release agents, coloring agents such as carbon black, phthalocyanine blue, phthalocyanine green and the like.

Thermosetting resin compositions of the present invention can be obtained by uniformly mixing various components as described above in a predetermined ratio. The mixing can be carried out by hot-melting these components at a desired temperature 20 to 100° C. higher than the softening point thereof.

The mixing can also be carried out by uniformly dispersing or dissolving various components of a thermosetting resin composition together. Solvents are not particularly limited, but examples that can be used include toluene, xylene, methylethylketone, methylisobutylketone, dioxane, methyl cellosolve, dimethylformamide and the like. These solvents may be used in an amount of generally 5 to 300 parts by weight, more preferably 10 to 150 parts by weight per 100 parts by weight of resin content.

Further, thermosetting resin compositions of the present invention can be suitably used for fabricating laminated sheets having a low dielectric constant. Since laminated sheets necessitate flame retardant properties, it is desirable to blend as a curing agent compounds containing a halogen in the molecule thereof or to blend the halogenated epoxy resins so that the resulting cured products may have a bromine content of generally 10 to 40% by weight, preferably 12 to 35% by weight, more preferably 15 to 27% by weight. Such laminated sheets can be fabricated by the steps of: dissolving a thermosetting resin composition of the present invention in a solvent so as to form a varnish; impregnating or coating the obtained varnish into or onto a substrate selected from glass cloth, non-woven glass fabric, synthetic fiber, paper, etc.; heating and drying the varnish-impregnated or varnish-coated substrate so as to form a prepreg by removing the solvent; superposing a desired number of prepreg sheets so as to form a laminate; overlaying a copper foil on one or each face of the obtained laminate; and applying heat and pressure to the resulting laminate for curing the composition of the present invention. Suitable solvents are toluene, xylene, acetone, methylethylketone, methylisobutylketone, dimethylformamide, etc. and may be used in such an amount that the solvents may be present in a proportion of generally 10 to 70% by weight, preferably 15 to 65% by weight of the mixture of the composition of the present invention with the solvent.

When polyhydric phenol compounds of the present invention are intended to be used as starting materials of thermoplastics, known processes similar to those for conventional phenol compounds can be applied.

EXAMPLES

The present invention will now be described in more detail by way of examples, which are by no means limitative. In the following examples, epoxy equivalent, softening point, saponifiable chlorine content, melt viscosity and melting point were measured under the following conditions. In the description hereinafter, part denotes part by weight.
(1) Epoxy equivalent: measured by a method in accordance with JIS K-7236.
(2) Softening point: measured by a method in accordance with JIS K-7234.
(3) Saponifiable chlorine content: determined by adding iN solution of KOH in ethanol to a solution of a sample in dioxane, allowing the resulting mixture to reflux for 30 minutes, measuring the evolved chlorine by silver nitrate titration and dividing the measured value by the weight of the sample.
(4) melt viscosity: measured by the cone plate method at 150° C.
   Measuring instrument: cone plate (ICI) pyroviscometer (fabricated by RESEARCH EQUIPMENT (LONDON) LTD.)
   Cone No. 3 (measurement range: 0 to 20 P)
   Weight of a sample: 0.15±0.01 g
(5) melting point: measured-by a DSC analysis at a temperature rise rate of 10° C./min.

EXAMPLE A1

Into 244 parts of 2,6-xylenol and 122 parts of methanol placed in a flask equipped with a stirrer and a reflux condenser, 7 parts of sodium hydroxide were added and dissolved with stirring. When the resulting mixture was heated to reflux, 96 parts of furfural was added dropwise under reflux over 2 hours. Then the mixture was allowed to react for 15 hours at the reflux temperature and neutralized with 140 parts of 20% aqueous sodium dihydrogenphosphate. 500 parts of water was added thereto. Precipitated crystals were collected by filtration, washed with 1:1 methanol/water and dried in a vacuum drying oven. This procedure yielded 304 parts of polyhydric phenol compound of the present invention (P1) represented by the formula (5):

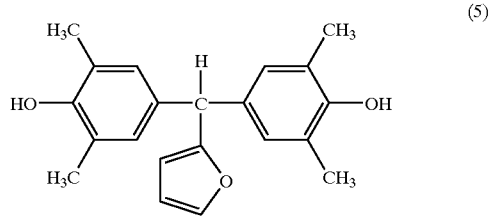

melting point: 147° C. $^1$H-NMR spectrum (CDCl$_3$, 300 MHz): shown in FIG. 1.

EXAMPLE A2

Figure 2:
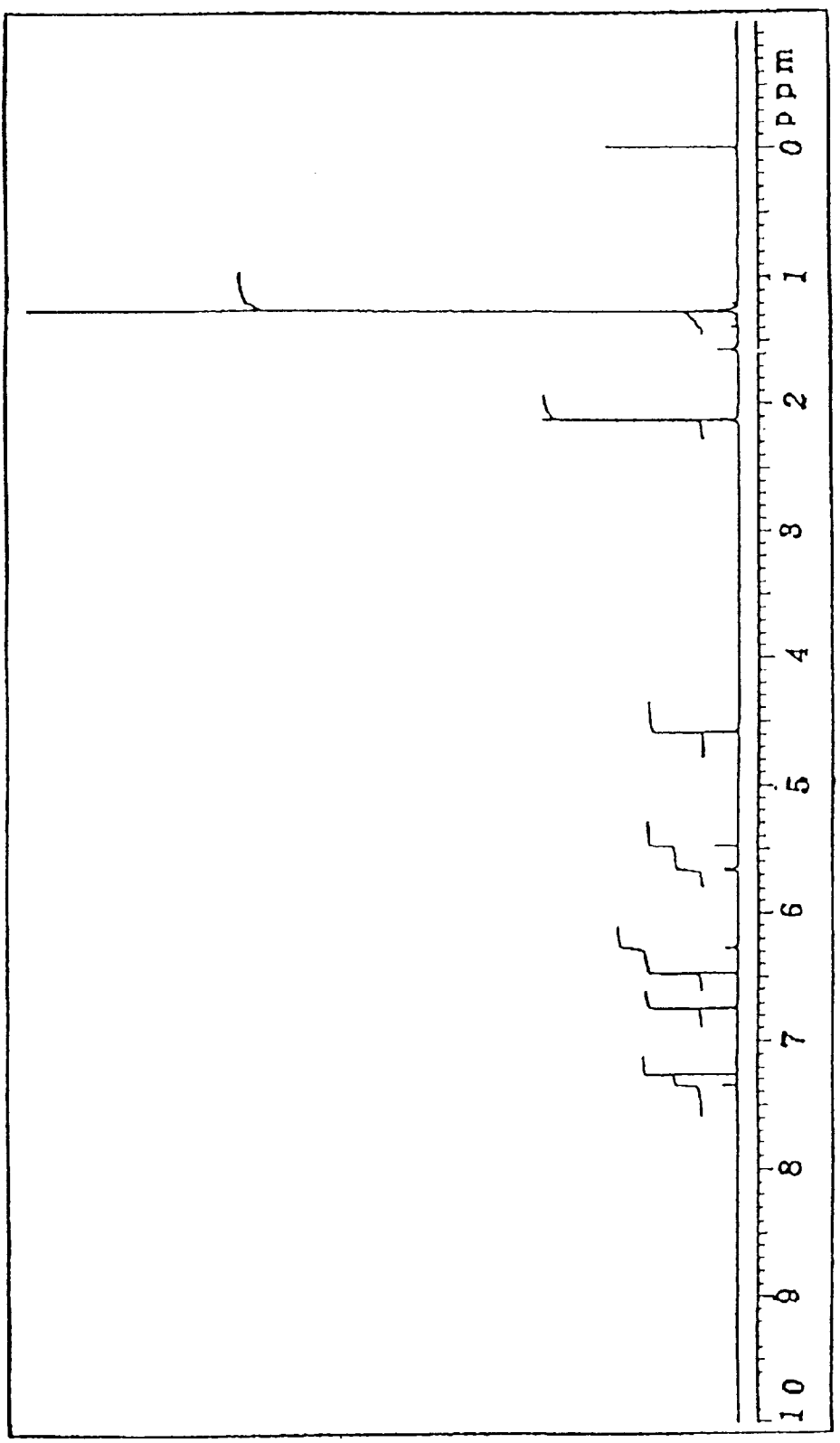
FIG. 2 represents the $^1$H-NMR spectra of the polyhydric phenol compound of the present invention (P2) obtained in Example A2.

Into 328 parts of methanol and 328 parts of 2-tert-butyl-5-methylphenol placed in a flask equipped with a stirrer and a reflux condenser, 4 parts of sodium hydroxide were added and dissolved by stirring. When the resulting mixture was heated to reflux, 96 parts of furfural were added dropwise under reflux over 2 hours. Then, 36 parts of sodium hydroxide was added at the rate of 4 parts every 2 hours while allowing to proceed the reaction at the reflux temperature. After the reaction was allowed to continue for 35 hours from the end of addition of furfural, 240 parts of methanol and 240 parts of water were added to the reaction mixture, which was in turn neutralized with 200 parts of 35% aqueous hydrochloric acid. Precipitated crystals were collected by filtration, washed with a solution of 2:1 methanol/water, washed again with methanol and dried in a vacuum drying oven. This procedure yielded 332 parts of polyhydric phenol compound of the present invention (P2) represented by the formula (6):

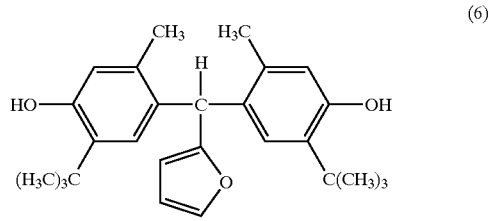

melting point: 236 to 237° C. $^1$H-NMR spectrum (CDCl$_3$, 300 MHz): shown in FIG. 2.

EXAMPLE A3

Into 113 parts of phenol and 28 parts of methanol placed in a flask equipped with a stirrer and a reflux condenser, 12 parts of sodium hydroxide were added and dissolved by stirring. When the resulting mixture was heated to reflux, 29 parts of furfural were added dropwise under reflux over 2 hours. Then, the mixture was allowed to react for 20 hours at the reflux temperature and neutralized with 30 parts of 35% aqueous hydrochloric acid. 5 parts of 80% hydrazine were added thereto. Then, 150 parts of methylisobutylketone were added, the resulting mixture was washed with water repeatedly and unreacted phenol and methylisobutylketone were distilled off under heating in vacuum, to obtain 332 parts of polyhydric phenol compound of the present invention (P3) represented by the formula (7):

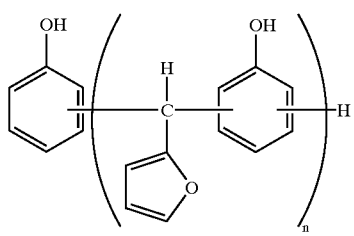

(7)

wherein n is 3.1 (average value). The obtained polyhydric phenol compound had a softening point of 92° C. and a melt viscosity of 5.1 P.

EXAMPLE A4

The procedure of Example A1 was repeated, except that 244 parts of 2,6-xylenol were replaced with 244 parts of 2,5-xylenol, to obtain 301 parts of polyhydric phenol compound of the present invention (P4) represented by the formula (8):

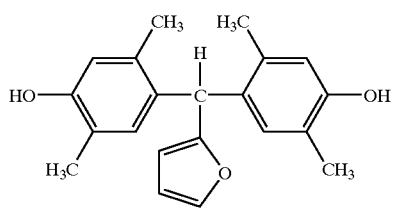

(8)

The obtained polyhydric phenol compound had a melting point of 192° C.

EXAMPLE A5

The procedure of Example A1 was repeated, except that 244 parts of 2,6-xylenol were replaced with 272 parts of 2,3,6-trimethyl phenol and sodium hydroxide was replaced with 5 parts of lithium hydroxide, to obtain 298 parts of polyhydric phenol compound of the present invention (P5) represented by the formula (9):

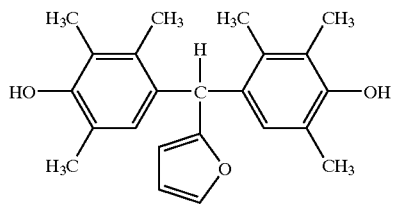

(9)

The obtained polyhydric phenol compound had a melting point of 176° C.

EXAMPLE A6

The procedure of Example A1 was repeated, except that sodium hydroxide was replaced with 5 parts of lithium hydroxide, furfural was replaced with 112 parts of 2-thiophenecarboxyaldehyde and the reaction time was increased to 25 hours, to obtain 307 parts of polyhydric phenol compound of the present invention (P6) represented by the formula (10):

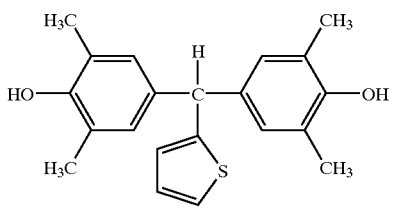

(10)

The obtained polyhydric phenol compound had a melting point of 167° C.

EXAMPLE A7

The procedure of Example A6 was repeated, except that 244 parts of 2,6-xylenol were replaced with 244 parts of 2,5-xylenol and the reaction time was increased to 30 hours, to obtain 284 parts of polyhydric phenol compound of the present invention (P7) represented by the formula (11):

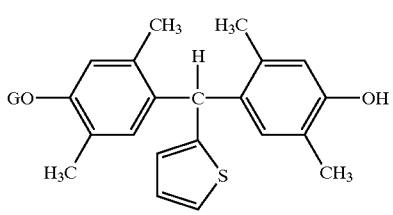

(11)

The obtained polyhydric phenol compound had a melting point of 216° C.

EXAMPLE A8

The procedure of Example A6 was repeated, except that 244 parts of 2,6-xylenol were replaced with 272 parts of 2,3,6-trimethyl phenol and the reaction time was increased to 60 hours, to obtain 284 parts of polyhydric phenol compound (P8) of the present invention represented by the formula (12):

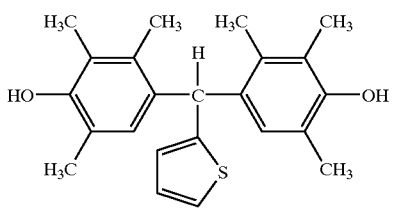

(12)

The obtained polyhydric phenol compound had a melting point of 163° C.

EXAMPLE A9 to A11

100 parts of o-cresol novolak epoxy resin (E1) (EOCN-1020 fabricated by Nihon Kayaku Inc.; epoxy equivalent: 198g/eq.; softening point: 65° C.) were blended with one of the polyhydric phenol compounds (P1)~(P3) of the present invention in such amounts as indicated in Table 1 and 1 part of cure accelerator (triphenylphosphine). The resulting mixture was kneaded with a twin roll, subjected to grinding and tableting, then passed through a transfer molding machine at 175° C. for 180 seconds to obtain a molded resin, which in turn was allowed to cure at 180° C. for 8 hours, to obtain a cured product of the present invention. Properties of the resulting cured product were examined under conditions as set forth below and the results are shown in Table 1.

glass transition temperature (TMA): was measured by TM-7000 supplied from Shinku Riko Inc. at a temperature rise rate of 2° C./min;

water absorption: was determined by measuring the weight increase (%) of a test piece in the form of a disk having 5 cm diameter ×4 mm thickness after boiled in water of 100° C. for 24 hours;

Copper foil peeling strength: was measured in accordance with the method described in JIS C-6481 (peeling strength);

Izod impact test: carried out in accordance with JIS K7710.

TABLE 1

| Ex. | A9 | A10 | A11 |
| --- | --- | --- | --- |
| Type of curing agent | P1 | P2 | P3 |
| Weight (part) of curing agent | 134 | 169 | 133 |
| Glass transition temp. (° C.) | 132 | 130 | 149 |
| Water absorption (%) | 1.02 | 0.99 | 1.13 |
| Copper foil peeling strength (Kg/cm) | 2.5 | 2.6 | 2.5 |
| Izod (KJ/mm$^2$) | 21 | 23 | 17 |

EXAMPLE B1

161 parts of polyhydric phenol compound (P1) obtained in Example A1 ywere placed in a reaction container and 500 parts of epichAorohydrin (hereinafter referred to as ECH) and 100 parts of dimethylsulfoxide (hereinafter referred to as DMSO) w ere add ed thereto. After the resulting mixture was dissolved by heating and stirring, 100 parts of 40 w/t % aqueous sodium hydroxide was added dropwise to the reaction system continuously over 4 hours while keeping the temperature at 45° C. and the pressure within the reaction system at 45 Torr. Water and ECH were azeotropically distilled out. After the distillate was cooled to separate into ECH and water, only the organic layer that was containing ECH was recycled to the reaction system while the reaction was allowed to continue. After the end of dropwise addition of aqueous sodium hydroxide, the reaction mixture was allowed to react at 45° C. for 3 hours, then 70° C. for another 30 minutes. Then, the mixture was repeatedly washed with water to remove by-produced salts and dimethylsulfoxide. After the excess of epichlorohydrin was distilled off from the oily phase by heating in vacuum, the residue was dissolved by adding 500 parts of methylisobutylketone.

The resulting methylisobutylketone solution was heated to 70° C., 4 parts of 30 % aqueous sodium hydroxide was added thereto and the resulting mixture was allowed to react for 1 hour. Thereafter, the reaction solution was repeatedly washed with water until the washing liquid became neutral. Then, methylisobutylketone was distilled off from the oily layer by heating in vacuum, to obtain 210 parts of an epoxy resin of the present invention (E1) represented by the formula (13):

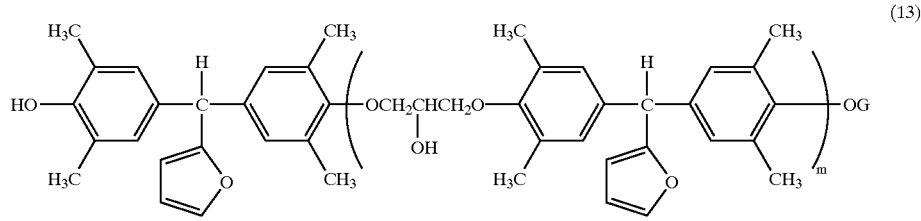

(13)

wherein G represents a glycidyl group; and m is 0.03 (average value). The epoxy resin (E1) had an epoxy equivalent of 222 g/eq., a softening point of 45° C., a melt viscosity of 0.4 P and a saponifiable chlorine content of 370 ppm.

EXAMPLE B2

The procedure of Example B1 was repeated, except that 161 parts of polyhydric phenol compound (P1) of Example B1 were replaced with 203 parts of polyhydric phenol compound (P2) obtained in Example A2 as well as an amount of ECH was changed to 650 parts and an amount of DMSO was changed to 120 parts. This procedure yielded 245 parts of an epoxy resin of the present invention (E2) represented by the formula (14):

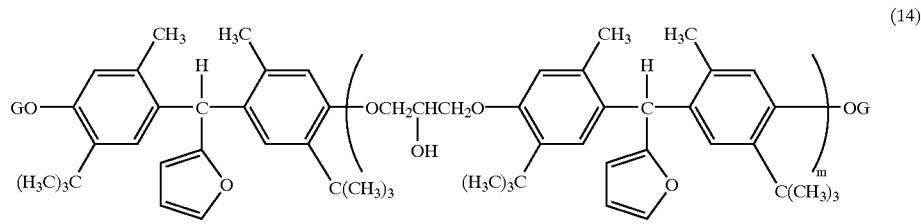

(14)

wherein G represents a glycidyl group; and m is 0.04 (average value). The epoxy resin (E2) had an epoxy equivalent of 270 g/eq., a softening point of 68° C., a melt viscosity of 0.4 P and a saponifiable chlorine content of 360 ppm.

EXAMPLE B3

The procedure of Example B1 was repeated, except that 161 parts of polyhydric phenol compound (P1) of Example B1 were replaced with 133 parts of polyhydric phenol compound (P3) obtained in Example A3 as well as an amount of ECH was changed to 400 parts and an amount of DMSO was changed to 100 parts. This procedure yielded 170 parts of an epoxy resin of the present invention (E3) represented by the formula (15):

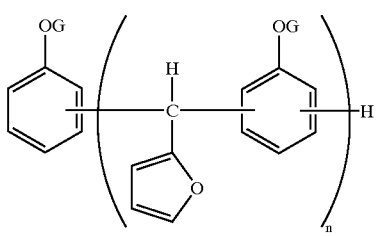

(15)

wherein G represents a glycidyl group; and m is 4.9 (average value). The epoxy resin (E3) had an epoxy equivalent of 225 g/eq., a softening point of 65° C., a melt-viscosity of 3.6 P and a saponifiable chlorine content of 410 ppm.

EXAMPLE B4

Into 56 parts of phenol and 28 parts of methanol placed in a flask equipped with a stirrer and a reflux condenser, 2 parts of sodium hydroxide were added and dissolved by stirring. When the resulting mixture was heated to reflux, 29 parts of furfural were added dropwise under reflux over 2 hours. Then, the mixture was allowed to react for 20 hours at the reflux temperature (80° C. to 90° C.) and 250 parts of epichlorohydrin were added thereto. To the resulting mixture, 12 parts of flaky sodium hydroxide were added continuously over 1 hour at 70° C. After the end of addition of sodium hydroxide, the reaction mixture was allowed to react for 1 hour at 70° C. Then, the reaction mixture was repeatedly washed with water to remove by-produced salts and methanol. After the excess of epichlorohydrin was distilled off from the oily phase by heating in vacuum, the residue was dissolved by adding 300 parts of methylisobutylketone.

The resulting methylisobutylketone solution was heated to 70° C., 4 parts of 30 w/t % aqueous sodium hydroxide were added thereto and the resulting mixture was allowed to react for 1 hour. Thereafter, the reaction solution was repeatedly washed with water until the washing liquid became neutral. Then, methylisobutylketone was distilled off from the oily layer by heating in vacuum, to obtain 70 parts of an epoxy resin (E4) of the present invention represented by the formula (15) set forth above wherein n is 4.9 (average value). The epoxy resin (E4) had an epoxy equivalent of 240 g/eq., a softening point of 66° C., a melt viscosity of 2.3 P and a saponifiable chlorine content of 780 ppm.

EXAMPLE B5

The procedure of Example B1 was repeated, except that 161 parts of polyhydric phenol compound (P1) of Example B1 were replaced with 161 parts of polyhydric phenol compound (P4) obtained in Example A4. This procedure yielded 221 parts of an epoxy resin of the present invention (E5) represented by the formula (16):

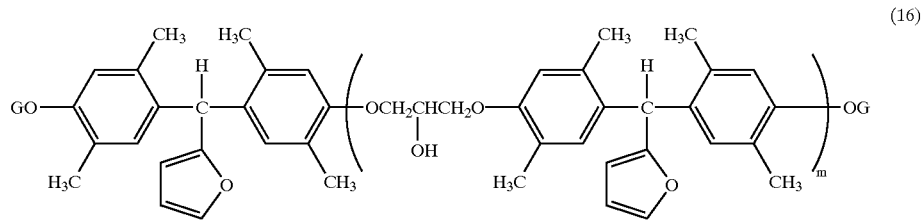

(16)

wherein G represents a glycidyl group; and m is 0.08 (average value). The epoxy resin (E5) had an epoxy equivalent of 232 g/eq., a softening point of 66° C., a melt viscosity of 0.5 P and a saponifiable chlorine content of 380 ppm.

EXAMPLE B6

The procedure of Example B1 was repeated, except that 161 parts of polyhydric phenol compound (P1) of Example B1 were replaced with 175 parts of polyhydric phenol compound (P5) obtained in Example A5. This procedure yielded 219 parts of an epoxy resin of the present invention (E6) represented by the formula (17):

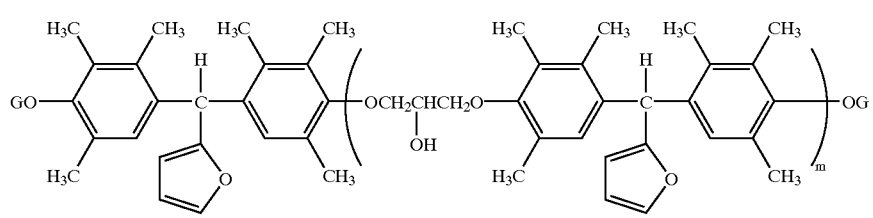

(17)

wherein G represents a glycidyl group; and m is 0.03 (average value). The epoxy resin (E6) had an epoxy equivalent of 238 g/eq., a softening point of 68° C., a melt viscosity of 1.0 poise and a saponifiable chlorine content of 370 ppm.

EXAMPLE B7

The procedure of Example B1 was repeated, except that 161 parts of polyhydric phenol compound (P1) of Example B1 were replaced with 169 parts of polyhydric phenol compound (P6) obtained in Example A6. This procedure yielded 216 parts of an epoxy resin of the present invention (E7) represented by the formula (18):

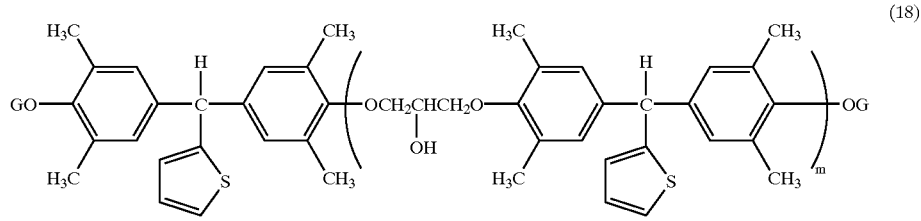

(18)

wherein G represents a glycidyl group; and m is 0.04 (average value). The epoxy resin (E7) had an epoxy equivalent of 233 g/eq., a softening point of 50° C., a melt viscosity of 0.4 P and a saponifiable chlorine content of 400 ppm.

EXAMPLE B8

The procedure of Example B1 was repeated, except that 161 parts of polyhydric phenol compound (P1) of Example B1 were replaced with 169 parts of polyhydric phenol compound (P7) obtained in Example A7. This procedure yielded 214 parts of an epoxy resin of the present invention (E8) represented by the formula (19):

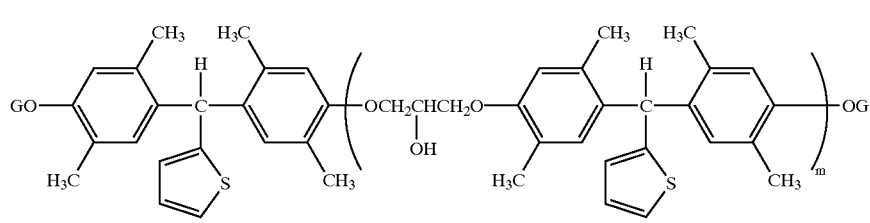

(19)

wherein G represents a glycidyl group; and m is 0.07 (average value). The epoxy resin (E8) had an epoxy equivalent of 239 g/eq., a softening point of 71° C., a melt viscosity of 0.6 P and a saponifiable chlorine content of 390 ppm.

EXAMPLE B9

The procedure of Example B1 was repeated, except that 161 parts of polyhydric phenol compound (P1) of Example B1 were replaced with 183 parts of polyhydric phenol compound (P8) obtained in Example A8. This procedure yielded 214 parts of an epoxy resin of the present invention (E9) represented by the formula (20):

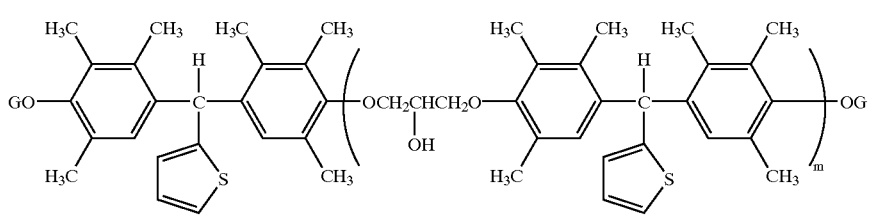

(20)

wherein G represents a glycidyl group; and m is 0.04 (average value). The epoxy resin (E9) had an epoxy equivalent of 248 g/eq., a softening point of 74° C., a melt viscosity of 1.4 P and a saponifiable chlorine content of 410 ppm.

EXAMPLE B10 to B18

A curing agent (phenolic novolak resin, PN-80 fabricated by Nippon Kayaku Inc.; melt viscosity at 150° C.: 1.5 poises; softening point: 86° C. and hydroxyl equivalent: 106g/eq.) was blended with each of epoxy resins (E1)–(E9) obtained in Examples B1 to B9 in an mount of 1 hydroxyl equivalent per 1 epoxy equivalent and further 1 part of cure accelerator (triphenylphosphine) per 100 parts of the epoxy resin was added. The resulting mixture was passed through a transfer molding machine to form a molded resin, which was then allowed to cure at 160° C. for 2 hours and 180° C. for another 8 hours.

Physical properties of the obtained cured products were examined and the results are shown in Tables 2 and 3.

Physical properties were determined by the following method:
- Water absorption: measured in the same way as was described in Example A9 to A11;
- Copper foil peeling strength: measured by 180° peeling test.
  - measuring temperature: 30° C.;
  - tensile testing speed: 200 mm/min.
  - copper foil: 70 μm JTC foil; supplied by Nikko Gourd Inc.;
- Izod impact test: carried out in the same way as described in Example A9 to A11.

TABLE 2

| Ex. | B10 | B11 | B12 | B13 | B14 |
|---|---|---|---|---|---|
| Epoxy resin | E1 | E2 | E3 | E4 | E5 |
| Water absorption (%) | 1.2 | 1.1 | 1.3 | 1.2 | 1.2 |
| Copper foil peeling strength (Kg/cm) | 2.8 | 2.6 | 2.4 | 2.5 | 2.9 |
| Izod (KJ/cm) | 23 | 14 | 11 | 13 | 13 |

TABLE 3

| Ex. | B15 | B16 | B17 | B18 |
|---|---|---|---|---|
| Epoxy resin | E6 | E7 | E8 | E9 |
| Water absorption (%) | 1.1 | 1.1 | 1.0 | 1.2 |
| Copper foil peeling strength (Kg/cm) | 2.7 | 2.7 | 2.7 | 2.7 |
| Izod (KJ/cm) | 20 | 24 | 17 | 13 |

Polyhydric phenol compounds of the present invention are suitable for use in various kinds of plastic materials (polycarbonate, PEEK, PPO, polysulfone, etc.), thermosetting resin materials (epoxy resin, cyanate resin, acrylate resin, etc.), antioxidants, insulating materials for electric and electronic parts including highly reliable sealing compounds for semiconductors, various composite materials including laminated sheets (printed-wiring boards) and CFRP (carbon fiber-reinforced plastics), components of adhesive compositions, coating compositions and molding compositions as well as various industrial intermediates. The process of the present invention can provide polyhydric phenol compounds of the present invention at a reasonable cost, while diminishing the production of by-products.

Epoxy resins of the present invention, by virtue of having a high moisture resistance (water resistance), a high impact resistance and good adhesive properties in the form of cured products, are extremely suitable for use in insulating materials for electric and electronic parts including highly reliable sealing compounds for semiconductors, various composite materials including laminated sheets (printed-wiring boards) and CFRP, components of adhesive compositions and coating compositions and the like. In particular, sealing compounds for semiconductors incorporating the epoxy resins of the present invention exhibit a good resistance to solder cracking.

What is claimed is:

1. A thermosetting resin composition comprising a polyhydric phenol compound represented by the formula (1):

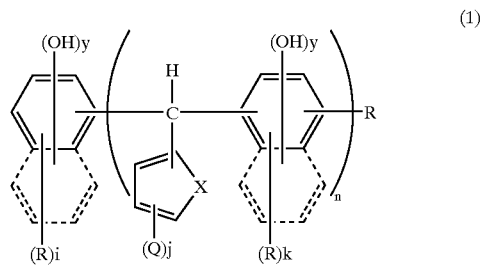

(1)

wherein X represents an oxygen or sulfur atom; Q represents a hydrogen atom or a C1–C5 alkyl group; R represents a hydrogen atom, a C1–C10 hydrocarbon group, an alkoxy group or a halogen atom; i is an integer of 1 to 6; j is an integer of 1 to 3; k is an integer of 1 to 5; and y is an integer of 1 to 2; and n is an average number and represents a real number of 1 to 15.

2. An epoxy resin represented by the formula (3):

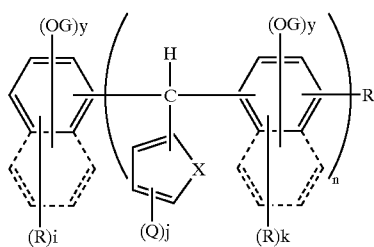
(3)

wherein G represents a glycidyl group, X represents an oxygen or sulfur atom: Q represents a hydrogen atom or a C1–C5 alkyl group: R represents a hydrogen atom, a C1–C10 hydrocarbon group, an alkoxy group or a halogen atom: i is an integer of 1 to 6; j is an integer of 1 to 3; k is an integer of 1 to 5; y is an integer of 1 to 2: and n is an average number and represents a real number of 1 to 15.

3. An epoxy resin represented by the formula (4):

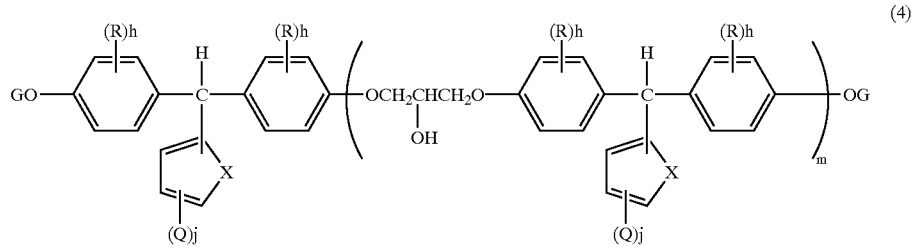
(4)

wherein G represents a glycidyl group X represents an oxygen or sulfur atom: Q represents a hydrogen atom or a C1–C5 alkl group: R represents a hydrogen atom, a C1–C10 hydrocarbon group, an alkoxy group or a halogen atom, j is an integer of 1 to 3; m is an average value and represents a real number of 0 to 20; and h represents an integer of 1 to 4.

4. A thermosetting resin composition comprising an epoxy resin as represented by the formula (3) or (4):

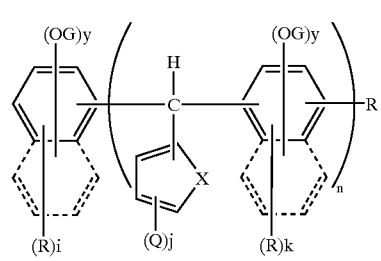
(3)

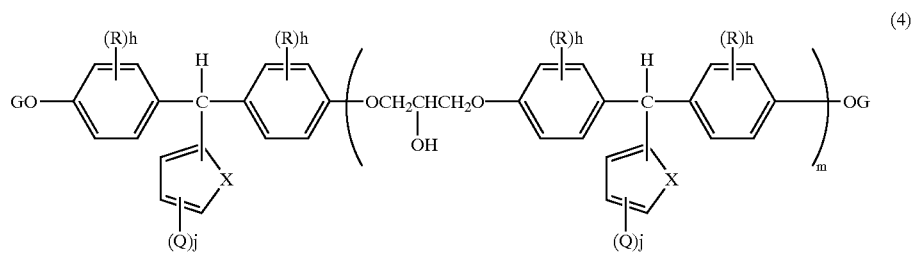
(4)

wherein G represents a glycidyl group and R, Q, X, n, y, i, j and k have the same meaning as defined in formula (1), and m is an average value and represents a real number of 0 to 20, and h represents an integer of 1 to 4.

5. A thermosetting resin composition comprising a polyhydric phenol compound represented by the formula (1):

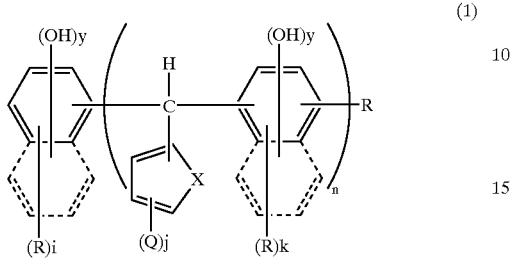

(1)

wherein X represents an oxygen or sulfuir atom; Q represents a hydrogen atom or a C1–C5 alkyl group; R represents a hydrogen atom, a C1–C10 hydrocarbon group, an alkoxy group or a halogen atom; i is an integer of 1 to 6; j is an integer of 1 to 3; k is an integer of 1 to 5; and y is an integer of 1 to 2; n is an average number and represents a real number of 1 to 15, and an epoxy resin as represented by the formula (3) or (4):

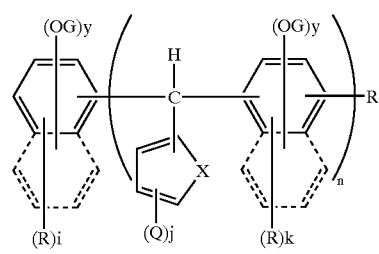

(3)

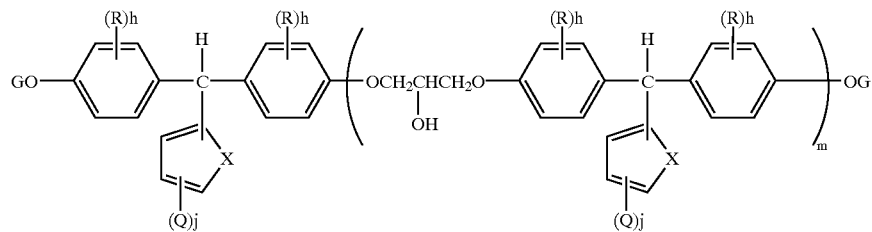

(4)

wherein G represents a glycidyl group and R, Q, X, n, y, i, j and k have the same meaning as defined in formula (1), and m is an average value and represents a real number of 0 to 20, and h represents an integer of 1 to 4.

6. A cured product obtained by curing the thermosetting resin composition as claimed in any one of claims 1, 4 or 5.

7. A semiconductor device comprising the thermosetting resin composition as claimed in any one of claims 1, 4 or 5 as a sealing material.

* * * * *